United States Patent
Pagano et al.

(10) Patent No.: US 7,054,762 B2
(45) Date of Patent: *May 30, 2006

(54) METHOD AND SYSTEM FOR ANALYSIS OF ULTRASONIC REFLECTIONS IN REAL TIME

(75) Inventors: Dominick A. Pagano, Weston, CT (US); John Winkelman, Southbury, CT (US); John Rojas, Norwalk, CT (US); James Norris, Danbury, CT (US)

(73) Assignee: Dapco Industries Inc., Ridgefield, CT (US)

( * ) Notice: Subject to any disclaimer, the term of this patent is extended or adjusted under 35 U.S.C. 154(b) by 226 days.

This patent is subject to a terminal disclaimer.

(21) Appl. No.: 10/652,279

(22) Filed: Aug. 28, 2003

(65) Prior Publication Data

US 2004/0113625 A1    Jun. 17, 2004

Related U.S. Application Data

(60) Provisional application No. 60/406,842, filed on Aug. 29, 2002.

(51) Int. Cl.
*G01V 3/08* (2006.01)

(52) U.S. Cl. .................................................. 702/39
(58) Field of Classification Search ............ 702/33–35, 702/39, 81, 109, 159
See application file for complete search history.

(56) References Cited

U.S. PATENT DOCUMENTS

| 4,222,275 A | * | 9/1980 | Sholl et al. ................... 73/636 |
| 4,593,569 A | * | 6/1986 | Joy ............................. 73/636 |
| 5,777,891 A | * | 7/1998 | Pagano et al. ................ 702/39 |

* cited by examiner

*Primary Examiner*—John Barlow
*Assistant Examiner*—Cindy D. Khuu
(74) *Attorney, Agent, or Firm*—Dickstein, Shapiro, Morin & Oshinsky, LLP.

(57) ABSTRACT

An ultrasonic real-time inspection method which is user-friendly in an interactive environment to provide ease of operation, as well as a combination of consistency, thoroughness, and speed of operation in flaw detection not achievable by other methods. The method offers significantly increased pattern recognition capability, which provides greater automation potential and reduced missed detection and false alarm rates.

46 Claims, 10 Drawing Sheets

METHOD AND SYSTEM FOR ANALYSIS OF ULTRASONIC REFLECTIONS IN REAL TIME

This application claims priority from provisional application Ser. No. 60/406,842, filed Aug. 29, 2002, which is hereby incorporated by reference in its entirety.

FIELD OF THE INVENTION

This invention relates to real-time ultrasonic non-destructive testing systems and methods. More particularly, to systems and methods that offer advances in real-time ultrasonic pattern recognition. It is applicable for use in systems to test the integrity of railroad rails, and other elongatedd material.

BACKGROUND

U.S. Pat. No. 5,777,891 by Pagano et al (hereinafter the "'891 patent"), hereby incorporated by reference as if fully disclosed herein, teaches ultrasonic real-time inspection methods which are user-friendly, interactive, as well as providing a combination of consistency, thoroughness, and speed of operation in flaw detection not achievable by methods previously known.

The methods taught by the '891 patent offer significantly increased pattern recognition capability compared to the prior art, and have greater automation potential and reduced missed detection and false alarm rates. The methods taught by the '891 patent are adaptable for use in a rail inspection system for examining railroad rails for flaws and identifying flaws in the rail in real-time. The rail inspection system repetitively and regularly injects pulses of ultrasonic beams into the rails from test devices mounted on a vehicle traveling along the rails. Acoustic echoes caused at rail discontinuities (such as a joint in the rails) are detected within the test devices to produce electrical signals representative of the magnitude of the acoustic echoes. The travel times of the acoustic echoes to the place of injection are determined, and deriving from the travel times, angles of travel, beam pulse speeds, and beam spreads of the ultrasonic beams inside the rails, spatial signals representative of the locations of the discontinuities along the rails are obtained. The system then combines spatial signals located within the rails to identify and locate flaws in and along the rails. Information representative of normal patterns of known rail discontinuities, are stored by the system. This information is compared to the combined spatial signals to detect and identify unknown discontinuities (which are flaws) and to eliminate and reclassify those discontinuities inconsistent with recognized context, and indicating the locations of said rail discontinuities.

It is an objective of the instant invention to expand and improve on the teachings of the '891 patent, by providing a novel method for differentiating ultrasonic reflections during real-time analysis in an ultrasonic inspection system.

It is another object of the invention to provide a method for using pattern recognition rules to detect and classify indications in real-time non-destructive testing.

It is a related object to provide tools for the building, analysis and management of these pattern recognition rules.

It is a further object of the invention to provide methods for recognizing indications in the test article by using a multi-stage decomposition analysis process.

It is another object of the invention to provide an easily adaptable system that can be adapted for different test conditions.

Another object is to utilize algorithms based on a two-phase analysis to provide context-sensitive analysis against a sequence of test data. A related object is to utilize the algorithms for finding and classifying anomalies from an input data set, and to sort data based on certain criteria.

SUMMARY

The above and related objects are achieved by providing methods applicable for use in ultrasonic real-time non-destructive inspection systems. As utilized in a preferred embodiment, it is adaptable for use in a system for the ultrasonic inspection of railroad rails ("Rail Inspection System"). However, it is applicable to any general scheme to perform real-time pattern recognition operations.

In most prior-art pattern recognition systems, data is located and analyzed only after it is processed. Under the novel approach of the instant invention, data is analyzed in a first-stage as it is gathered, by sensing the order in which the data is being received. The data is then analyzed in subsequent steps to obtain a high degree of accuracy.

BRIEF DESCRIPTION OF THE DRAWINGS

The foregoing and other advantages and features of the invention will become more apparent from the detailed description of exemplary embodiments provided below with reference to the accompanying drawings in which.

DETAILED DESCRIPTION

In the following detailed description, reference is made to the accompanying drawings, which are a part of the specification, and in which is shown by way of illustration various embodiments whereby the invention may be practiced. These embodiments are described in sufficient detail to enable those skilled in the art to make and use the invention. It is to be understood that other embodiments may be utilized, and that structural, logical, and electrical changes, as well as changes in the materials used, may be made without departing from the spirit and scope of the present invention.

Ultrasonic non-destructive rail testing involves the use of ultrasonics to test the steel of a rail, without damaging the rail in the test process. This technique relies on the ability of the ultrasonic vibrations to propagate through the material, and to reflect off of discontinuities such as voids or cracks in the material. Ultrasonics is the use of sound waves which have a frequency which is higher than an adult human is able to hear (greater than 20,000 cycles per second). In many ways, ultrasonic testing is similar to the use of radar or sonar, in that reflections of the sound energy can be used to detect or identify targets or "features". Just as a light beam will reflect off of a wall, a beam of sound energy will reflect off of a discontinuity in the medium (e.g., the material, the steel of the rail). In some instances, the reflection will be a normal rail feature, such as the bottom of the rail, a normal bolt hole, or a rail end. In such cases, the feature is considered "normal" and the reflection is not reported as an anomalous condition. The skill in ultrasonic testing lies in discriminating between normal features such as the bottom of rail, and abnormal conditions, such as voids in the rail structure.

If a beam of sound is sent directly into the rail (zero degrees from the vertical), it will be reflected off the bottom of the rail and an "echo" will be seen by the detection equipment. This is an expected condition and the lack of this expected response, termed "LER", is useful information since it indicates that either the sound beam has been obstructed by some other discontinuity, or that there is not adequate "coupling" of the sound energy into the steel. Another feature which is often detected, is a reflection from the underside of the head in the fillet area of the rail. The strength of this echo is highly dependent on the alignment of the test probe on the rail is useful in maintaining proper alignment of the equipment.

Many defects are oriented nearly vertically in the rail and often will not give a significant echo to the zero degree beam traveling vertically down through the rail. In order to detect these defects, it is necessary to use a number of directional beams at various angles, each looking for particular features in the rail. A beam of 45 degrees from the vertical detects cracks which propagate from bolt holes. A 70 degree beam detects transverse defects in the head area.

Accurate sizing of defects is important in order for the railroad to determine the severity of the defective rails. Due to the wide variation of the amount of sound energy transmitted into the rail caused by constantly changing conditions such as worn and rusty rails, grease on the rail, etc., the amplitude of reflected signal is not a useful characteristic to use. Transmissions of the sound beam are made at fixed intervals based on movement of the test vehicle. The equipment looks at the number of successive echoes received from a feature and uses this information to give an indication of the size of defects.

The following descriptions about the invention is applicable to a Rail Inspection System as disclosed in the '891 patent. In the preferred embodiment, the System comprises: A Vehicle, such as an automotive van; Wheel Probe Carriage attached to the Vehicle; Ultrasonic Wheel Probes; two or three for each rail, mounted on the carriage; Liquid Couplant System included in the Vehicle and Carriage; and an ultrasonic-based, computerized, Flaw Detection/Recognition System. The Vehicle houses and provides support and power for the entire Rail Inspection System. The Wheel Probe Carriage is carried either under the rear deck of the vehicle, or folded up into the rear compartment, and provides an adjustable surface for mounting of the wheel probes which carry the ultrasonic transducers. Two or three Wheel Probes are provided for each rail. Each wheel probe consists of a set of ultrasonic transducers mounted axially and contained within a fluid-filled wheel, which rolls on the rail surface. Each wheel probe has a leading transducer fixed at an angle to the horizontal, a zero degree transducer pointing straight at the rail, and a trailing transducer at an angle.

Figure 1:
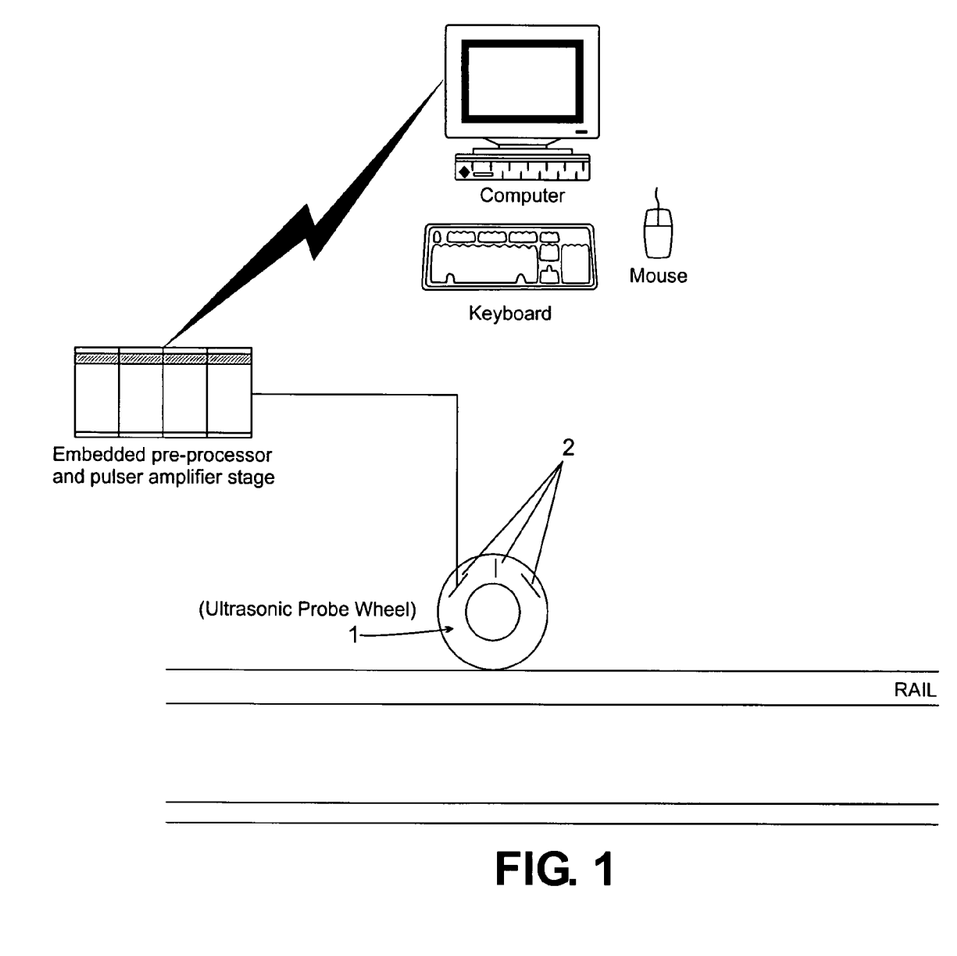
FIG. 1 shows a generalized apparatus to measure walk direction.

Now referring to the figures, where like reference numbers designate like elements, FIG. 1 shows a generalized apparatus incorporating an Ultrasonic Wheel Probe 1 with a plurality of ultrasonic transducers 2 mounted at angles to measure the "walk direction." The "walk direction" is defined as the movement direction, based upon time response, of successive ultrasonic reflections from a given feature in the rail. These features may indicate a flaw (such as a cracked rail), or a normal condition (such as a bolt hole). It is possible to use the walk direction, in combination with other parameters (e.g., angle of the transducer; transducer orientation relative to direction of motion of the item under inspection; and direction of travel), to determine if a successive collection of ultrasonic reflections from a given indication is a reflection from that indication or a multi-path reflection from a different indication or indications. This is crucial for pinpointing the actual location/depth of the indication.

Figure 2:
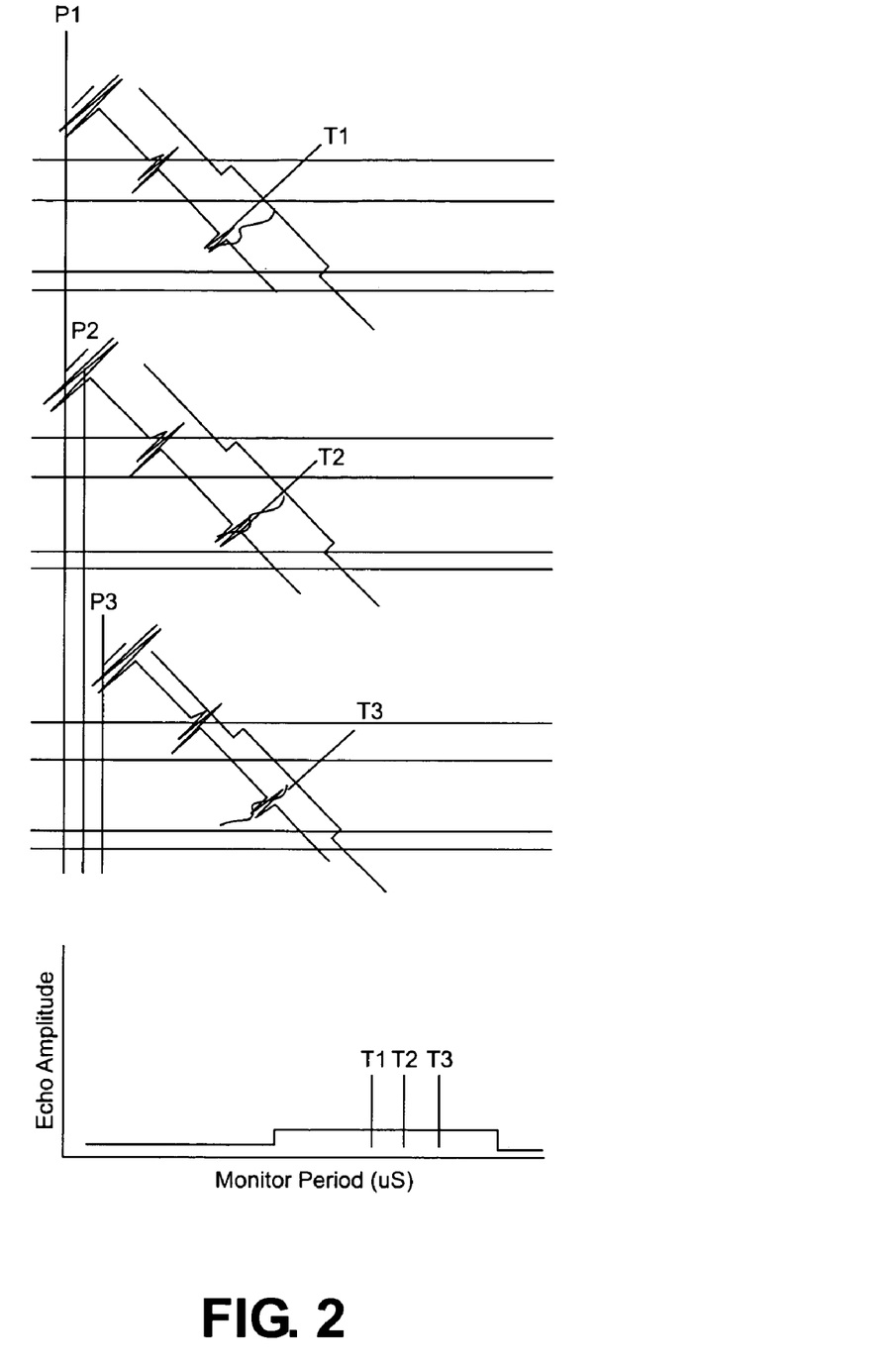
FIG. 2 illustrates a method of determining walk direction in accordance with an exemplary embodiment of the invention.

Referring to FIG. 2, as the location of the ultrasonic echo is tracked over multiple ultrasonic transducer firings at T1, T2 and T3 as it traverses positions P1, P2 and P3, an echo moving out in time (i.e., a greater echo response time) is designated as walking in the "positive" direction. An ultrasonic echo tracked over multiple transducer firings that exhibits decreasing response times is designated as exhibiting a "negative" walk. By knowing the orientation of the ultrasonic transducers and the direction of motion it is possible to determine if the walk represents a reflection from a rail anomaly or is a multiple signal (a reflection that has bounced off of multiple surfaces), a surface wave (in the case of a 70 degree transducer) or a single point reflection off of a rail anomaly.

A walk direction can have one of three characteristics:
a. "Not walking" for a reflective surface that maintains a constant response time separation from the transducer over multiple pulsing cycles (stays the same distance from the transducer).
b. Positive walk for a reflective surface that has an increasing response time separation from the ultrasonic transducer over multiple pulsing cycles (falling away from the transducer).
c. Negative walk for a reflective surface that has a decreasing response time separation from the ultrasonic transducer over a multiple pulsing cycles (moving closer to the transducer).

An invalid walk direction is one that, due to the orientation of the transducer, the direction of motion and the orientation of the reflective surface relative to the transducer, produces a series of responses that are not physically possible. The is because an ultrasonic pulse, much like a radar pulse, produces an energy wave that over time propagates away from the transducer and into the target media, in this case steel. When that pulse encounters a surface, that surface reflects the ultrasonic energy. The orientation of the surface determines that angle at which the ultrasonic energy is reflected. If the angle of incidence (the angle at which the ultrasonic pulse strikes the surface) exceeds the critical angle of reflection (the angle at which no energy is reflected back to the transducer), all of the ultrasonic energy will be reflected in such a way that none of the reflected energy is returned to the transducer. Because the critical angle is known, the direction of travel of the transducer and the orientation of the transducer, it is possible to determine if the responses are in fact possible.

FIGS. 3*a*–3*d* show a transducer pulse-echo response over four pulsing cycles. In each figure, the same circular reflective surface 10 typical of a bolt hole in the rail lying parallel to the ground, and an ultrasonic transducer 100 is shown. A series of pulses #1 (FIG. 3*a*), #2 (FIG. 3*b*), #3 (FIG. 3*c*) and #4 (FIG. 3*d*) are fired with the direction of motion of the transducer going from right to left. During the first pulsing cycle the transducer 100 is pulsed and an ultrasonic pulse 110 is fired. The echo strikes the surface 10 at a position such that the ultrasonic energy 120 is reflected away from the transducer 100. The energy is reflected away because the tangent 20 to the surface of the circle 10 at the point of contact exceeds the critical angle of reflection (see FIG. 3*e*).

During the second pulsing cycle the transducer 100 is pulsed and energy traveling along path 110 strikes the surface of reflective surface 10 at such an angle that the angle of incidence 30 allows for some ultrasonic energy 120 to be returned to the transducer 100 and a signal is detected. The distance that the signal travels is calculated as the sum of the time of flight of the signal from the transducer to the reflective surface and back (200 in FIG. 3*e*).

During the third pulsing cycle, the transducer 100 is again pulsed and energy traveling along path 110 strikes the surface of reflective surface 10 in such a way that the angle of incidence 40 equals the angle of reflection and all of the ultrasonic energy is reflected back to the transducer along path 120. The distance that the signal travels is again calculated from the transducer to the reflective surface and back again (210 in FIG. 3*e*).

Figure 3:
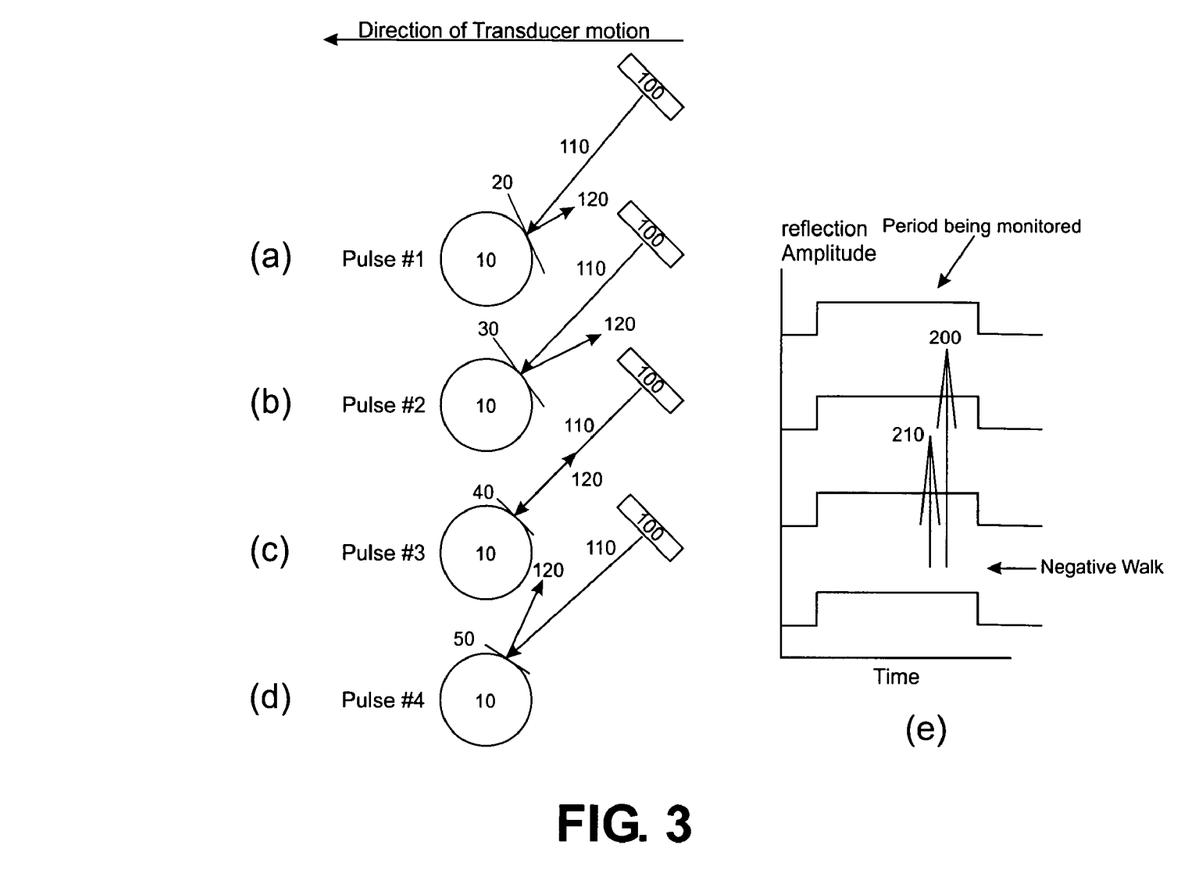
FIG. 3 shows a transducer pulse-echo response over four cycles.

During the fourth pulsing cycle, the transducer 100 is pulsed and another ultrasonic pulse 110 is fired. The pulse strikes the surface 10 at a position such that the ultrasonic energy 120 is reflected away from the transducer 100. The energy is reflected away because the tangent 50 to the surface of the circle 10 at the point of contact exceeds the critical angle of reflection.

The walk direction, then, must be negative for a transducer traveling from right to left with this orientation. No other walk direction is possible because no signal will be returned. Further, in the event that the direction of travel is opposite, that is from left to right, the walk direction must always be positive.

If, during the first pulsing cycle (i.e., pulse #1), the return echo were to strike another reflective surface, return to the circular surface 10 that in turn reflected it back to the transducer 100, the signal would be detected (as opposed to the undetected signal illustrated in FIGS. 3*a* and 3*e*). The time of flight of the signal would be very large. As such, the walk would appear to be in the positive direction. This is not physically possible for a transducer with this orientation and this direction of travel. The object of the invention is to eliminate false readings from other indications, in order to pinpoint the location of the indication (e.g., a fault in the rail). By knowing the orientation of the ultrasonic transducers and the direction of travel, it is possible to determine if the walk represents a reflection from a rail anomaly, or is a multi-path signal, a surface wave, or a single point reflection.

Determination of walk direction is accomplished by both hardware and software components. The walk direction is tracked by storing and tracking the echo location within the monitored area over multiple pulse-echo cycles. The walk direction is tracked by the hardware and then used by a pattern analysis system (described below) for tackling recognition problems. These problems may include: differentiating surface wave reflections from the ends of rails from transverse defects occurring near rail ends; differentiating multi-path reflections between a bolt-hole and rail end from a defective bolt-hole on the end portion of a rail joint; and differentiating normal pitting in the rails from oblique/transverse/horizontal defects.

The Rail Inspection System, traversing the rails to be examined, sends ultrasonic pulses at intervals into the rails from the transducers and receives the bounced back signals. Spatial transformation is performed on the received signals, in which sequential responses received by each transducer are plotted on a graph (refer to the '891 patent, incorporated as if fully disclosed herein, for a discussion of the Spatial Transformation operation). The software component of the novel and improved real-time ultrasonic inspection system comprises tools for the examination and evaluation of these graphs, which allows for the dynamic creation and evaluation of recognition rules that are subsequently used in the run-time system described below.

Figure 4:
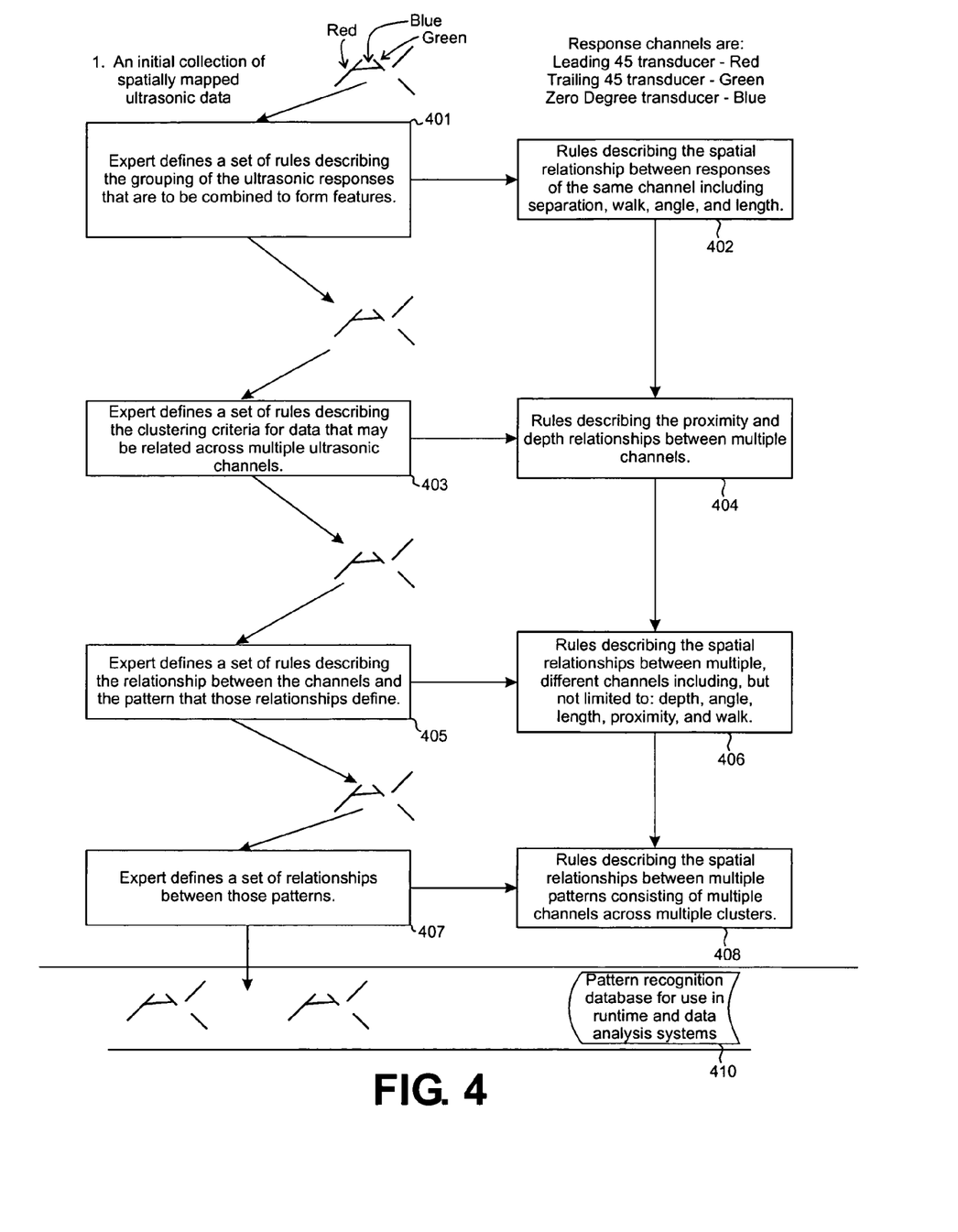
FIG. 4 illustrates a method for generating a set of rules in accordance with an exemplary embodiment of the invention.

Utilizing these tools, a set of rules can be generated for the responses for each transducer. Referring to FIG. 4, a first set of rules are defined according to the length of the response, the angle of the response, the walk direction and other criteria (401, 402). These rules define, in a general sense, what the ultrasonic response for typical features (e.g., bolts, rail ends, holes) would look like. This set of rules are saved to an expert rules database as "feature rules". These rules are utilized by a software test engine to perform real-time categorization of these typical rail features (bolts, rail ends, etc.).

Next, a second set of rules are generated relating to the proximity of certain rail features with their depth location in the rail under inspection (403, 404). These rules are saved to the expert rules database as "cluster rules." The cluster rules are retrieved by a run-time test engine and used to create clusters of related data for further analysis.

A further set of rules are generated relating to the feature rules previously generated. The features are related by the geometry of the defect and can include angle, length, walk direction and depth in the item under inspection (405, 406). These rules are saved in the expert rules database as "recognition rules" and are used by the run-time test engine to perform recognition of patterns of data within the item under inspection. Next, a set of rules relating the recognized patterns to each other (i.e., to other recognized patterns) are generated based on their order and spatial relationship (407, 408). These rules are saved as "context recognition rules" and are used by the test engine to recognize compound patterns of data within the item. The above steps can be repeated to refine the rules to create more precise rules describing the features in the rail. A pattern recognition database may be used to store all of the rules (410).

To assist the user to build, analyze, manage and refine the rules, a novel pattern recognition tool is provided that allows for the dynamic creation and evaluation of recognition rules in a real-time environment. The tool implements an interactive environment where an expert can evaluate ultrasonic pattern recognition algorithms through an intuitive user interface. The tool will allow the user to load and evaluate the rules against previously stored data sets. It can also be used to extract the rules from the reference data sets in order to alleviate the manual process of initially creating the rules. In this case, the user defines a type of indication, and the tool will create the rules needed to classify such an indication.

The tool can also be used to statistically compare a set of rules against a reference database of known indications, and report the results against previous comparisons. It can then be used to make specific adjustments to the rules in order to tighten or loosen the constraint parameters so that the comparison results will fit with required criteria.

In the preferred embodiment, these rules are generated and refined by an expert user of the rail inspection system, rather than by a programmer reviewing data in an abstract sense. The art of detecting flaws in rail is complicated by the fact that there are many features in the track that are intentionally put there (for example, bolt holes and bond pins). Those features can then have defects associated with them. Further, because rail inspection is such a specialized field, very little real research has been done into pattern recognition of rail using real data. Most research has grossly simplified the environment to provide possible scenarios of how certain, isolated anomalies may be detected. Dealing with the real environment where there are issues stemming from metallurgy, track geometry, track wear, and variable Federal definitions about what is a defect, is best supplemented with actual, irreplaceable human experience.

Once a rule has been established, it should not have to be changed dramatically. It may, however, need to be tweaked because of some exceptional boundary condition that has been discovered, or because of new kinds of rail geometry being encountered in a new market.

Once set, the set of rules are applied by a software test engine using real-time analysis methods which provide means for rapidly and efficiently analyzing the ultrasonic data as it is gathered. This novel method offers significant performance gains by breaking down the analysis phase into four discrete steps: feature recognition, cluster recognition, defect recognition, and context-based defect recognition. The process starts when a collection of ultrasonic responses from a given transducer is grouped into vectors called Defect Reports. The parameters that define a vector are: direction, length, and amplitude (or peak), along with each point that is part of the vector. The order in which the ultrasonic response was generated is maintained in the vector. The vector also keeps track of the channel type, and spatial location (x, y, z coordinate) of where the vector is located.

Figure 5:
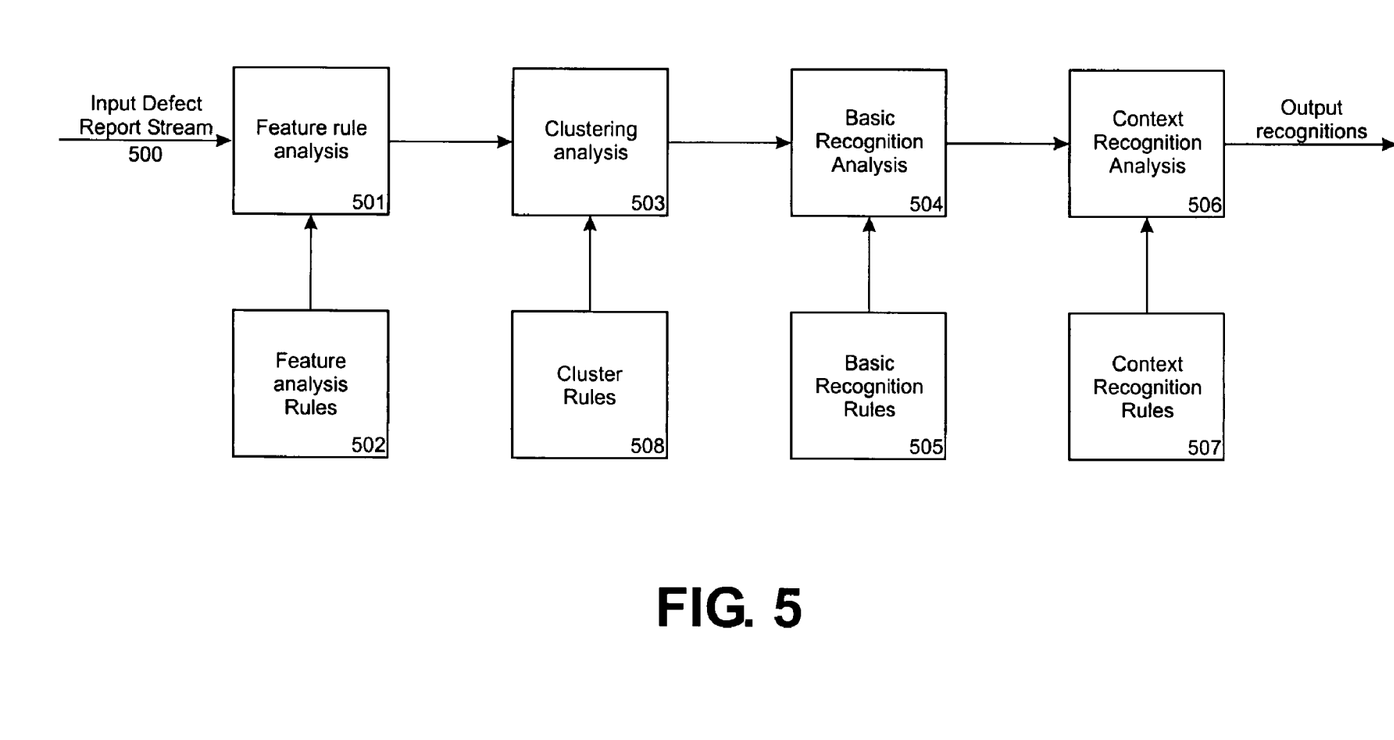
FIG. 5 illustrates analyzing ultrasonic data in accordance with an exemplary embodiment of the invention.
Figure 6:
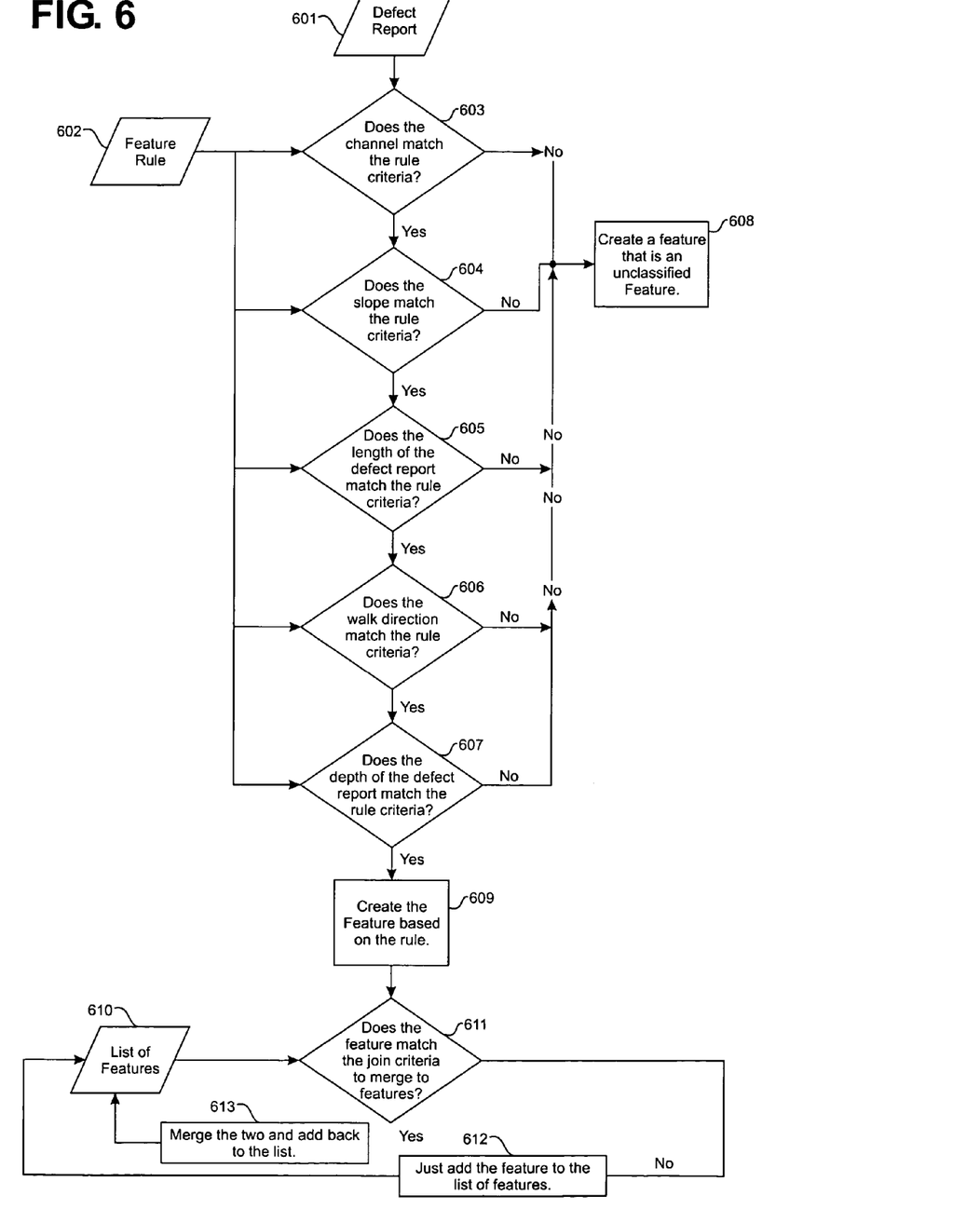
FIG. 6 illustrates a method of creating features from spatially transformed data based on certain criteria in accordance with an exemplary embodiment of the invention.

Referring to FIG. 5, the input defect stream 500 consists of Defect Reports from the embedded system containing the transducer/channel identifier (i.e., which transducer collected the data), the position at which the data was collected, the amplitude of the response and the position of the response in the rail (depth and position). The feature rule analysis stage 501, utilizing the feature analysis rules 502 compiled as discussed above, processes the input stream 500 along with the feature analysis rules to provide: (1) Joined feature data; and (2) Feature classification. The feature rules 502 are applied to a method for creating features from spatially transformed data based on certain criteria, as depicted in FIG. 6.

The feature rules (602) are applied to the Defect Report (601). Does the channel match the rule criteria(603)? Does the slope match the rule criteria (604)? Does the length of the defect report match the rule criteria (605)? Does the walk direction match the rule criteria (606)? Does the depth of the defect match the rule criteria (607)? Based on these criteria, either a feature that is henceforth unclassified (608) or a known feature (609) is identified. If the feature is known (611), does it match the criteria to merge back into the known list of features (613, 610) or should it be added to the list (612, 610)?

Figure 7:
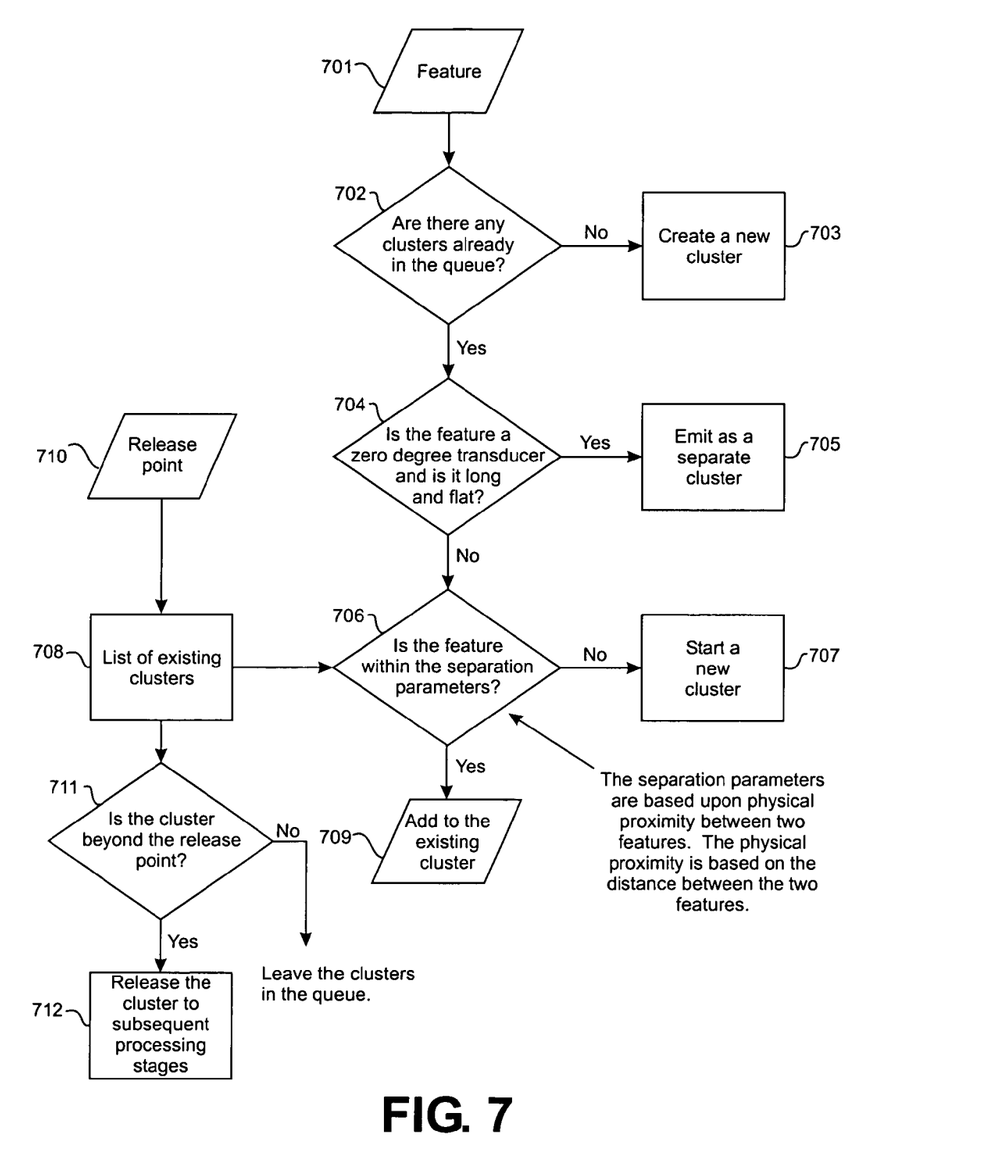
FIG. 7 illustrates a method of clustering data based upon certain criteria in accordance with an exemplary embodiment of the invention.

Referring again to FIG. 5, the output from the feature rule analysis stage 501 described above is then fed to the clustering analysis stage 503 so that the various features can be associated and subsequently processed by the basic recognition analysis stage 504 using cluster rules 508. Referring now to FIG. 7, in step (701) a feature is presented to the cluster analysis stage. If there are no other clusters in the list of clusters (702), a new cluster is created (703) and added to the cluster queue. If there are clusters in the queue (702), and the feature is "long" (user defined) and a flat response from a zero degree transducer (704), a new cluster is created and immediately released (705). If the feature is not long and flat (704), the feature is checked against each of the features in the list of clusters that are in the process of being built (706). If the spatial constraints are not satisfied then a new cluster is started (707) and added to the queue of clusters that are in process. If one or more spatial constraints are satisfied (706), then the feature is added to the first cluster that satisfied the constraint (709).

The satisfaction criteria (706) is defined by the user. Typically, the conditions are based upon physical proximity (based on the distance between two features). Additionally, if the condition is satisfied, then that cluster is compared to every other cluster in the queue. If the spatial parameters are satisfied, then the two clusters are combined. Periodically, the system feeds a release point to the cluster list (710). The release point is an indication to the system that all possible features up to that point in the test have been collected. The system then compares the release point to the maximum point for each cluster in the list (708, 711). If the maximum point for the cluster is less than the release point, the cluster is deemed complete and released to subsequent processing steps in the system (712), discussed below.

Referring again to FIG. 5, the output from the clustering analysis stage 503 is fed into the basic recognition analysis stage 504 where the clusters of features are processed to produce defect and real element classifications (such as bolt holes, transverse defects, etc.) using basic recognition rules 505. The output from the basic recognition analysis stage 504 is fed into the context recognition stage 506 where higher level recognition analysis is performed using content recognition rules 507 (recognition of patterns that are composed, themselves, of other recognitions).

Figure 8:
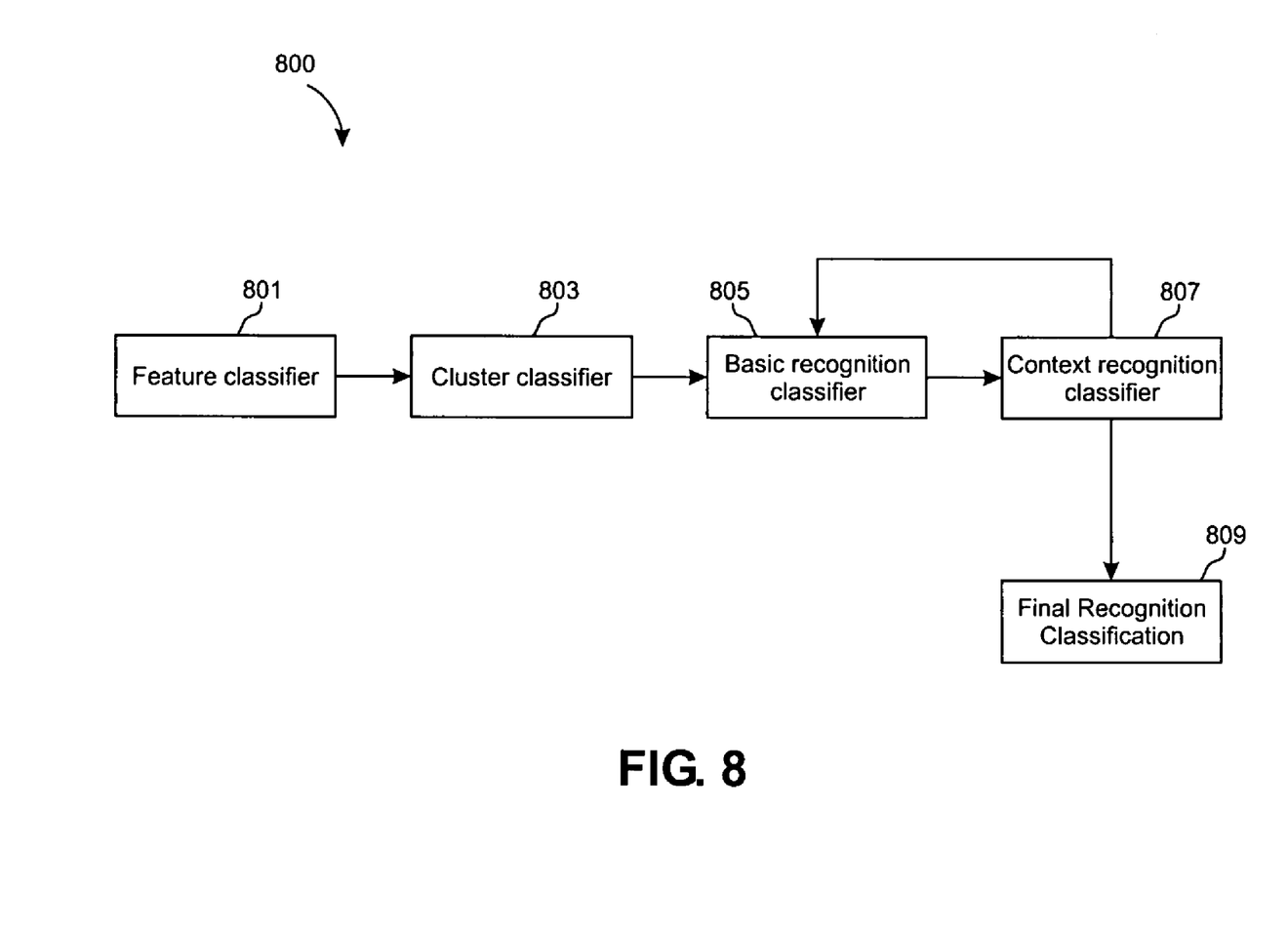
FIG. 8 illustrates a technique for performing context analysis against a sequence of test data in accordance with an exemplary embodiment of the invention.

FIG. 8 illustrates a method 800 for performing context analysis against a sequence of test data in accordance with an exemplary embodiment of the invention. The method 800 provides a means of recognizing large rail structure such as rail joints, switches and "frogs." The exemplary method is implemented by providing a state machine whose behavior is governed by a set of rules input by an expert in the field of ultrasonic inspection. The expert inputs the rules for the series of patterns to be analyzed. The patterns may be defined as a series of high level recognitions as well as series of unclassified lower level features. The system considers the previous data (hence the state machine) as well as the current input item (feature or recognition) in determining the final output.

Once the vectors are classified into features (801), the features are organized into cluster depending upon their proximity (803). The basic recognition classifier (805) decomposes the clusters into basic recognitions (805). The context recognition classifier (807) collects the basic recognitions and infers complex structures based upon the sequence of recognitions (807). The context recognition classifier (807) can re-submit an individual recognition for classification along with some information about its context for "re-recognition" or for final recognition classification (809).

Thus, the method 800 for doing context recognition is based on a two phase analysis. The first phase consists of a rule based state machine that examines recognized patterns in spatially sequence order. For example a rail joint may be recognized as two or more bolt holes, either normal or defective, followed by a transverse defect followed by two or more bolt holes. The application of the context recognizer is rules driven, where the rules are generated by an expert user rather than a programmer and are thus field modifiable.

The second component of the illustrated context recognition method 800 provides for feedback to the recognition stage with limiting rules defining the context in which a particular recognition as estimate to be incorrectly recognized. The method 800 provides additional information to the primary recognition stage that was not available during initial cluster analysis. Those rules are controlled by and defined by an expert user.

The illustrated method 800 provides a means of classifying defects contained within large rail structures that could not otherwise be classified. The method 800 is further advantageous due to its ability to allow for multiple structures to be nested (that is, complex defects mixed in with normal rail features that are themselves complex recognitions). The mechanism is implemented by allowing for parallel state machines to use the same overlapping data sets as well as share sub-state machines in the processing of the data.

The method 800 provides a means of re-classification based upon feedback to lower level stages. In the event that a state is reached where some portion of the data, once viewed in context, is deemed to have a high degree of error, that data along with the context information is fed back to a prior stage in the system for re-recognition. The stage that is performing the re-recognition utilizes the recognition context to re-interpret the data elements of the incorrectly recognized area and provide a most likely re-interpretation of the datum.

The method provides a means of associating multiple recognition to form complex patterns. The method also provides for a unique mechanism for doing feedback reclassification of basic rail anomalies based upon the surrounding recognitions. The method provides a unique mechanism for refining the recognition of large scale track structures (such as large defects, frogs, switches and rail joints) based upon the totality of the often disconnected data to generated a coherent recognition. The method provides a unique mechanism for classifying normal rail features, such as rail ends, that appear, out of context, to be defects.

This basic and context recognition stages 504, 506 (FIG. 5) provide a simple way of isolating the defective portion from the normally occurring portions of a recognized pattern within the material being tested. For example, in the case of a rail, bolt holes have normally occurring components that are recognized as a normal bolt hole pattern. When a bolt hole region also has a crack, the recognition is considered to be a compound recognition that includes both the normal bolt hole information along with the response data from the crack. By keeping all of the defective ultrasonic responses in a separate list, the system can present a more accurate representation of a defect.

Conventional systems will present a bolt hole and crack as a single defective indication. This is misleading, since the defect, in this case, is just the crack. The method of the invention solves this problem. When the size of a defect is reported, only the defective part is included in the measurement. This is more accurate than reporting the entire defect and anomaly together, even though it is still a relative value due to the nature of ultrasonics. This gives the ability of highlighting just the defective part of a cracked bolt hole, without highlighting the bolt hole itself. This would still work when the crack is on both sides of the bolt hole. It also provides a means of isolating the response data from the defect from the normally occurring responses (such as data from a bolt hole that is associated with a defect).

The method is driven by a set of recognition rules (see discussion above). Normally occurring responses will satisfy a recognition rule that has been crafted to detect the occurrence of the normally occurring condition. For example, a bolt hole in a rail is a normally occurring condition in a rail and a set of rules are constructed for detecting the occurrence of normal bolt holes. These patterns do not include responses that would classify the bolt hole as defective. The normally occurring responses are considered to be a "basic" recognition type. Basic recognitions are defined and processed prior to "compound" recognitions. A compound recognition is comprised of a basic recognition consisting of a set of expected responses along with the anomalous (non-expected) component.

Once a basic recognition has been detected, other ultrasonic responses in the area are then processed. If additional ultrasonic responses satisfy a rule that has been defined for a "compound" recognition, the basic recognition information and the ultrasonic responses for the anomalous component are each added to the recognition object in separate lists. This allows later processing stages to easily identify and process the anomalous part of the recognition. Since the anomalous component is identified, the length of the component can be calculated and the component can be highlighted within the recognition on a display.

Figure 9:
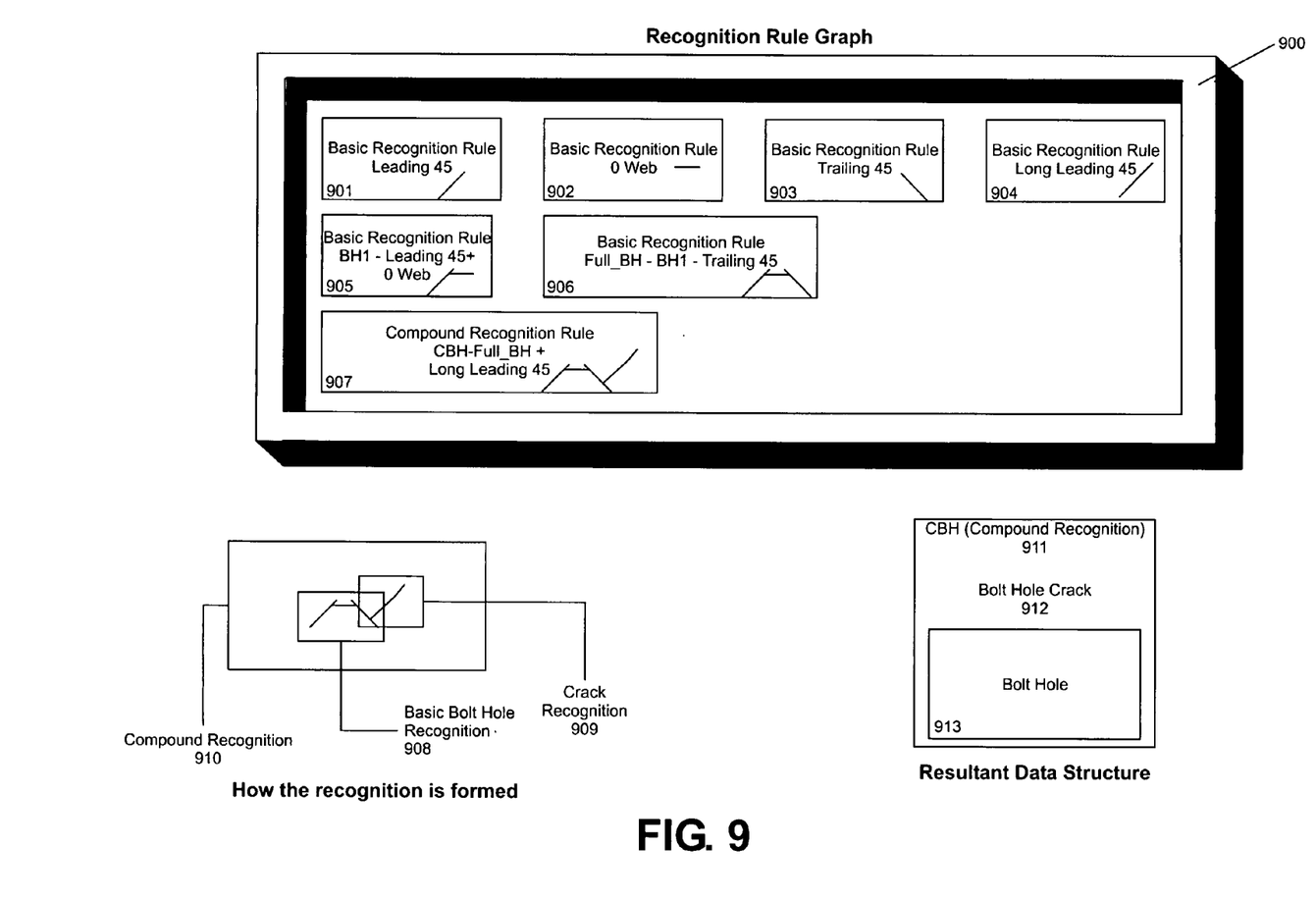
FIG. 9 illustrates the method of differentiating the anomalous part of an indication from the normally occurring parts of a recognized pattern.

FIG. 9 illustrates an exemplary process of the invention, using a cracked bolt hole as an example. When the recognition rules (900) are applied to the bolt hole area, and four basic recognition rules are satisfied: Leading 45 degree recognition (901), 0 degree web recognition (902), Trailing 45 degree recognition (903), and Long Leading 45 recognition (904). On the next pass, the simple basic recognitions are combined to form more complex basic recognitions. Recognitions (901) and (902) are combined to form basic recognition rule Bolt Hole ("BH1")(905). This basic recognition rule BH1 is combined with basic recognition rule (903) to form a more complex basic recognition (906), which defines a Full Bolt Hole ("Full-BH"). Once all of the basic recognitions have been identified, the next pass of the recognition process begins checking for compound recognitions. In this case the Full-BH basic recognition (906) and the Long Leading 45 basic recognition (904) are recognized as a Cracked Bolt Hole ("CBH") (907). The overall recognition is a compound recognition of many patterns (909, 910, 911). Within the compound recognition are the Full-BH basic recognition (908, 913) and the crack, which is recognized by the Long Leading 45 basic recognition (909, 912). The final output is then provided to the user for final decision.

Figure 10A:
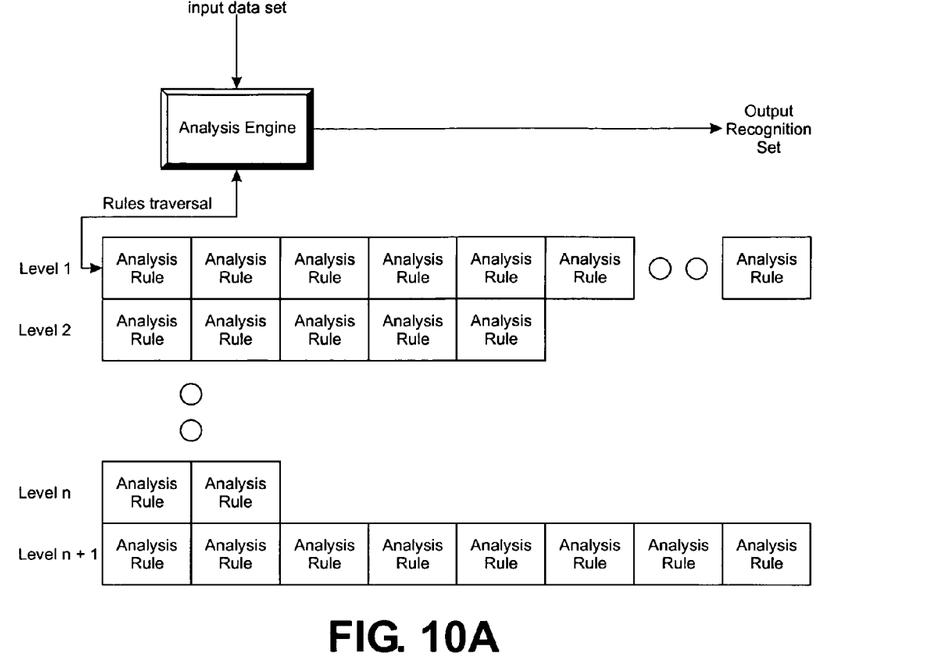
FIGS. 10a and 10b illustrate a technique for finding and classifying anomalies in accordance with an exemplary embodiment of the invention.
Figure 10B:
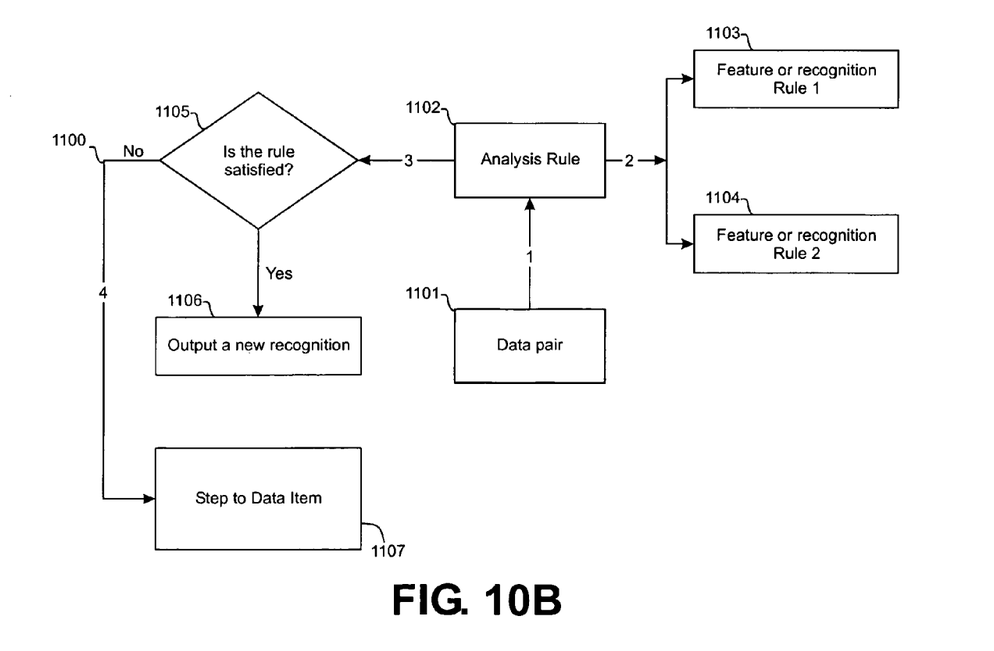

FIGS. 10*a* and 10*b* illustrate a method 1100 of finding and classifying anomalies in accordance with an exemplary embodiment of the invention. The method 1100 takes an input dataset and produces as its output collections of recognized rail patterns. The method 1100 implements an iterative process of analyzing ultrasonic features against predefined rules.

The algorithm is implemented using a set of user defined levels where each level may produce outputs that are used as inputs for subsequent levels (see e.g., FIG. 10a). In a preferred embodiment, the number of levels and the detail of analysis for each level are defined by an expert in the field of ultrasonic inspection.

The expert inputs the rules in a pair wise fashion indicating the order and rules for analysis. Each data pair may comprise a pair of features, a feature and a recognition or two recognitions. The analysis system invokes each rule (1103, 1104) against the entire input data set (1101, 1102). An analysis rule consists of the two recognition rules that must be satisfied to create a recognition. If the rule is satisfied (1105), then a new recognition is output (1106). Otherwise, the method proceeds to the next data item (1107). This way, the data is modified at each point in the valuation where the rule is satisfied. The modified data may then be used as part of the analysis in subsequent steps. Once the system has analyzed the data against all of the rules at all of the levels, it releases the resulting recognition set to the storage and presentation queues. The expert may define a varying number of rules for each level. The expert may define a varying number of levels.

Thus, the illustrated method 1100 provides an extensible mechanism for analyzing and categorizing ultrasonic responses into recognized patterns. The method 1100 is unique in that it interprets user-defined rules against a variable dataset to produce its output. The method 1100 implements an n-layer approach (FIG. 10a) that enables the rule-writer to build-up complex relationships by using a simple pair-wise comparison and analysis algorithm. The method 1100 implements a series of association rules based upon various kinds of proximity including specific points, shortest distance and all corners and three-dimensional relationships. The method 1100 implements: (1) a series of association rules based upon feature type; (2) association rules based upon depth in the rail (zone); and (3) an association interpreter to apply the dynamically generated rules.

In another embodiment the invention provides a method of associating classified test data with a rule (and/or a history of rules) used for classification. The method encompasses persisting the recognition mechanism (or path through the recognition tree) and allowing an informed expert or software package to analyze a resultant graph to tune for optimal flow and to eliminate dead or redundant paths through the graph.

This method provides the ability to determine what part of the calibration needs to be tuned in order to adjust a classification result. The method also provides statistical results indicating the type of recognitions that are being generated. For example, if there are fifty different kinds of cracked bolt holes, the system can provide information indicating which types are actually being found in the test medium. The method also provides a means of automatically generating statistics on flaw patterns in a rail. For example, the method can determine "what quadrant does a bolt hole most frequently crack for a certain type of rail?" As such, the method according to this exemplary embodiment provides a means of: (1) determining how a classification was done in a pattern recognition system; (2) tuning a recognition method based upon flow data through a recognition tree; (3) maintaining a recognition analyzer to eliminate dead portions of the graph; and (4) maintaining a recognition analyzer to detect and eliminate crossed or erroneous portions of a recognition graph.

The foregoing disclosure and description of the invention is illustrative and explanatory thereof, and various changes in the size, shape and materials, as well as in the details of the illustrated constructions, may be made within the scope of the appended claims, without departing from the spirit of the invention.

The processes and devices described above illustrate preferred methods and typical devices of many that could be used and produced. The above description and drawings illustrate embodiments, which achieve the objects, features, and advantages of the present invention. However, it is not intended that the present invention be strictly limited to the above-described and illustrated embodiments. Any modification, though presently unforeseeable, of the present invention that comes within the spirit and scope of the following claims should be considered part of the present invention.

For example, it is to be specifically understood that the invention and the following claims cover not only the analysis of railroad rails, but also are applicable to the analysis of any elongated material, such as tubular products, i.e., pipe and plate material. Thus, claim coverage herein is not to be construed as being limited only to rail inspection.

What is claimed as new and desired to be protected by Letters Patent of the United States is:

1. A method of performing real-time pattern recognition on an elongated material, said method comprising the steps of:
   injecting, using a test device, pulses of a plurality of ultrasonic beams into the elongated material;
   detecting acoustic responses caused at a discontinuity of the elongated material;
   determining a walk direction of the test device;
   determining at least one characteristic of the detected acoustic responses; and
   determining a pattern of a feature of the elongated material associated with said discontinuity based on the determined walk direction, the at least one characteristic and at least one pattern recognition rule.

2. The method of claim 1, wherein said at least one characteristic comprises a travel time.

3. The method of claim 1, wherein said at least one characteristic comprises an angle of travel.

4. The method of claim 1, wherein said at least one characteristic comprises a beam pulse speed.

5. The method of claim 1, wherein the walk direction comprises a positive walk direction.

6. The method of claim 1, wherein the walk direction comprises a negative walk direction.

7. The method of claim 1, wherein the walk direction comprises a non-walk direction.

8. The method of claim 1, wherein said step of determining the pattern comprises:
   classifying features associated with the responses;
   clustering the classified features;
   performing basic recognition analysis using the clustered classified features to determine a basic recognition; and
   performing context recognition analysis on the basic recognition to determine the pattern.

9. The method of claim 8, wherein said step of classifying features comprises:
   comparing the responses to a set of features rules; and
   deriving features based on the comparisons.

10. The method of claim 9, wherein the set of features rules are a set of rules developed by an expert.

11. The method of claim 8, wherein said step of clustering the classified features comprises:
    determining proximity relationships between the features;

comparing the proximity relationships to a set of clustering rules; and deriving clusters based on the results of the comparison.

12. The method of claim 11, wherein the set of clustering rules are a set of rules developed by an expert.

13. The method of claim 8, wherein said step of performing basic recognition analysis comprises:
comparing the clustered features to a set of basic recognition rules; and
deriving the basic recognition based on the results of the comparison.

14. The method of claim 13, wherein the set of basic recognition rules are a set of rules developed by an expert.

15. The method of claim 8, wherein said step of performing context recognition analysis comprises:
comparing the basic recognition to a set of pattern recognition rules; and
deriving the pattern based on the results of the comparison.

16. The method of claim 13, wherein the set of pattern recognition rules are a set of rules developed by an expert.

17. The method of claim 1, wherein the at least one pattern recognition rule comprises a multi-level expert-derived rule.

18. The method of claim 1, wherein the elongated material is a railroad rail and the pattern is a flaw in the rail.

19. The method of claim 1, wherein the elongated material is a railroad rail and the pattern is a feature of the rail, which is not defective.

20. The method of claim 1, wherein said pattern comprises multiple rail features.

21. A method of performing real-time pattern recognition on a railroad rail, said method comprising the steps of:
developing a set of pattern recognition rules associated with known discontinuities within the rail;
injecting, using a test device, pulses of a plurality of ultrasonic beams into the rail;
detecting acoustic responses caused at one or more discontinuities of the rail;
determining at least one characteristic of the detected acoustic responses; and
determining a pattern of at least one feature of the rail associated with the one or more discontinuities based on the at least one characteristic and at least one pattern recognition rule.

22. The method of claim 21, wherein said step of developing a set of pattern recognition rules comprises:
developing a set of features analysis rules;
developing a set of clustering analysis rules;
developing a set of basic recognition analysis rules; and
developing a set of context recognition analysis rules.

23. The method of claim 22, wherein said step of determining the pattern comprises:
classifying features associated with the responses based on said feature analysis rules;
clustering the classified features based on said clustering analysis rules;
performing basic recognition analysis using the clustered classified features to determine a basic recognition based on said basic recognition analysis rules; and
performing context recognition analysis on the basic recognition to determine the pattern of the feature based on the context recognition analysis rules.

24. The method of claim 22, wherein said rules are multi-level analysis rules.

25. The method of claim 21 further comprising:
determining a walk direction of the test device; and
using the determined walk direction to in determining the pattern.

26. The method of claim 25, wherein the walk direction comprises a positive walk direction.

27. The method of claim 25, wherein the walk direction comprises a negative walk direction.

28. The method of claim 25, wherein the walk direction comprises a non-walk direction.

29. The method of claim 21, wherein the pattern is a flaw in the rail.

30. The method of claim 21, wherein the pattern is a feature of the rail, which is not defective.

31. The method of claim 21, wherein the patter is an unknown flaw in the rail and said method further comprises the step of creating at least one rule associated with the unknown flaw.

32. The method of claim 21 further comprising the step of modifying the pattern recognition rules.

33. A system for performing real-time pattern recognition on an elongated material, said system comprising:
means for injecting pulses of a plurality of ultrasonic beams into the elongated material;
means for detecting acoustic responses caused at a discontinuity of the elongated material;
means for determining a walk direction of said injecting means;
means for determining at least one characteristic of the detected acoustic responses; and
means for determining a pattern of a feature of the elongated material associated with said discontinuity based on the determined walk direction, the at least one characteristic and at least one pattern recognition rule.

34. The system of claim 33, wherein said at least one characteristic is selected from the group consisting of travel time, angle of travel, and beam pulse speed.

35. The system of claim 33, wherein the walk direction comprises a positive walk direction.

36. The system of claim 33, wherein the walk direction comprises a negative walk direction.

37. The system of claim 33, wherein the walk direction comprises a non-walk direction.

38. The system of claim 33, wherein said means for determining the pattern comprises:
means for classifying features associated with the responses;
means for clustering the classified features;
means for performing basic recognition analysis using the clustered classified features to determine a basic recognition; and
means for performing context recognition analysis on the basic recognition to determine the pattern of the feature of the elongated material associated with said discontinuity.

39. The system of claim 38, wherein said classifying features means comprises:
means for comparing the responses to a set of features rules; and
means for deriving features based on the comparisons.

40. The system of claim 38, wherein said clustering means comprises:
means for determining proximity relationships between the features;
means for comparing the proximity relationships to a set of clustering rules; and means for deriving clusters based on the results of the comparison.

41. The system of claim 38, wherein said means for performing basic recognition analysis comprises:
   means for comparing the clustered features to a set of basic recognition rules; and
   means for deriving the basic recognition based on the results of the comparison.

42. The system of claim 38, wherein said means for performing context recognition analysis comprises:
   means for comparing the basic recognition to a set of pattern recognition rules; and
   means for deriving the pattern based on the results of the comparison.

43. The system of claim 33, wherein the at least one pattern recognition rule comprises a multi-level expert-based rule.

44. The system of claim 33, wherein the elongated material is a railroad rail and the pattern is a flaw in the rail.

45. The system of claim 33, wherein the elongated material is a railroad rail and the pattern is a feature of the rail, which is not defective.

46. A system for performing real-time pattern recognition on an railroad rail, said system comprising:
   a test device being adapted to ride on the rail, said test device injecting pulses of a plurality of ultrasonic beams into the rail and detecting acoustic responses caused at a discontinuity along the rail, said test device being programmed to determine a walk direction of said test device and at least one characteristic of the detected acoustic responses; and
   a processor, said processor being programmed to determine a pattern of a feature of the rail associated with said discontinuity based on the determined walk direction, the at least one characteristic and at least one pattern recognition rule.

* * * * *